United States Patent [19]

Janssen et al.

[11] Patent Number: 5,298,665

[45] Date of Patent: Mar. 29, 1994

[54] PROCESS FOR PREPARING AN ALKANONE AND/OR ALKANOL

[75] Inventors: Ludovicus H. W. Janssen, Geleen; Peter Hoogendoorn, Sittard; Ubaldus F. Kragten, Beek; Henricus A. C. Baur, Herten, all of Netherlands

[73] Assignee: DSM N.V., Netherlands

[21] Appl. No.: 31,469

[22] Filed: Mar. 15, 1993

Related U.S. Application Data

[63] Continuation of Ser. No. 857,409, Mar. 25, 1992, abandoned.

[30] Foreign Application Priority Data

Mar. 25, 1991 [NL] Netherlands .......................... 9100521

[51] Int. Cl.$^5$ .............................................. C07C 45/53
[52] U.S. Cl. .................................... 568/342; 568/311; 568/385; 568/835; 568/909.8
[58] Field of Search ............... 568/311, 385, 342, 835, 568/909.8

[56] References Cited

U.S. PATENT DOCUMENTS

| | | | |
|---|---|---|---|
| 2,497,349 | 2/1950 | Farkas et al. | 568/342 |
| 2,851,496 | 9/1958 | Cates et al. | 568/342 |
| 3,557,215 | 1/1971 | Bonnart et al. | 568/342 |
| 3,928,477 | 12/1975 | Field et al. | 568/385 |
| 4,076,759 | 2/1978 | Field et al. | 568/385 |
| 4,459,427 | 7/1984 | Middleton et al. | 568/385 |
| 4,482,752 | 11/1984 | Mitchell et al. | 585/670 |
| 4,490,566 | 12/1984 | Chang et al. | 568/385 |
| 4,898,987 | 2/1990 | Knifton | 568/385 |

FOREIGN PATENT DOCUMENTS

| | | | |
|---|---|---|---|
| 0096798 | 12/1983 | European Pat. Off. | 568/385 |
| 0180269 | 5/1986 | European Pat. Off. | 568/342 |
| 0367326 | 9/1990 | European Pat. Off. | 568/342 |
| 1530986 | 6/1968 | France | 568/385 |
| 1159006 | 7/1969 | United Kingdom | 568/385 |
| 1212824 | 11/1970 | United Kingdom | 568/342 |

OTHER PUBLICATIONS

A. C. Banciu et al.; Oxidation of Cumene With Molecular Oxygen in Presence of Co(II) Acetylacetonate Complexes Heterogenized on Silane Modified Silica; Revue Roumaine de Chimie, 34 (1989) 1711-1720.

Ichiro Okura et al.; On the kinetics and the Mechanism of Hydrogen Peroxide Decomposition With Silica—Supported Metallo-Porphyrins; Journal of Molecular Catalysis, 5, (1979) 293-301.

Yasuhiko Kurusu and D. C. Neckers; Functionalization of Silica Gel: Application for the Catalytic Oxidation of Alkanes; 914 The Journal of Organic Chemistry 56; (91991) 1981-1983.

European Search Report, Nov. 28, 1991.

Primary Examiner—James H. Reamer
Attorney, Agent, or Firm—Cushman, Darby & Cushman

[57] ABSTRACT

The invention relates to a process for preparing an alkanone and/or alkanol by oxidizing an alkane with 3-30 C-atoms, using oxygen, to form an alkyl hydroperoxide, followed by a decomposition of the resulting alkyl hydroperoxide in the presence of a metal compound immobilized on a carrier, which carrier carries aliphatic or aromatic amine groups or sulphide groups. The process is preferably applied to cycloalkanes.

21 Claims, No Drawings

PROCESS FOR PREPARING AN ALKANONE AND/OR ALKANOL

This is a continuation of application Ser. No. 07/857,409, filed Mar. 25, 1992, now abandoned.

FIELD OF THE INVENTION

The invention relates to a process for preparing an alkanone and/or alkanol by oxidizing an alkane, having from 3 to 30 C-atoms, and thereafter using oxygen to form an alkyl hydroperoxide, and the decomposing the resulting alkyl hydroperoxide in the presence of a metal compound immobilized on a carrier.

More particularly, the present invention relates to a process for preparing an alkanone and/or alkanol by decomposing an alkyl hydroperoxide in a solvent in the presence of a metal compound immobilized on a carrier, wherein the carrier contains aliphatic or aromatic amine groups or sulphide groups.

BACKGROUND OF THE INVENTION

According to EP-367326, a cyclohexane hydroperoxide obtained by air oxidation can be converted under a high yield into a corresponding ketone (or ketone, K) and an alcohol (or alkanol, A). In other literature, frequent attention is given to the oxidation of alkanes such as, for instance, cycloalkanes, particularly cyclohexane, to form a corresponding alkanol and/or alkanone. In such methods, two process steps can be distinguished: first of all, the conversion of the alkane into a mixture substantially containing the corresponding alkyl hydroperoxide, followed by a conversion (decomposition) of this alkyl hydroperoxide into a K/A mixture. In addition to the direct conversion of the alkyl hydroperoxide, in this second step the alkyl hydroperoxide frequently also reacts with the substantial amount of remaining alkane, which again results in the formation of K and A. In some cases, this so-called alkane participation plays an essential part in the total conversion of the alkane and the yield of the K/A mixture that goes with it.

The major difference between the oxidation step and the decomposition step is that the latter is performed at lower temperatures. The difference in temperature is at least 20° C., preferably at least 40° C. This may be because in the oxidation step, performed essentially without a catalyst, a relatively high temperature is maintained to keep an acceptable reaction rate; still relatively few products are formed. The decomposition step, in which a substantial amount of catalyst is used, would give rise to too many unwanted side products if performed at too high a temperature.

Many catalyst systems have been suggested for use in the above-mentioned process. GB 1212824, for instance, describes a homogeneous catalytic reduction of alkyl hydroperoxides. Homogeneous catalysis for the decomposition of alkyl hydroperoxides is still applied for commercial purposes, in spite of the formation of rather substantial catalyst waste streams. In order to avoid these waste streams, it has been suggested, as in U.S. Pat. No. 2,851,496, to absorb the catalyst on a carrier. However, the activity of such a catalyst has been found in course of time to deteriorate. Nor does the system described in EP-A-367326 (a Co-porphyrin complex, which porphyrin complex is linked with a carrier by means of a covalent bond) provide a stable catalyst active for a long time.

SUMMARY AND DESCRIPTION OF THE INVENTION

The present invention provides a process for the decomposition of alkyl hydroperoxides while utilizing the catalyst so that it retains its activity for a long period of time.

The present invention also provides a process for preparing an alkanone and/or alkanol by decomposing an alkyl hydroperoxide in the presence of a metal compound immobilized on a carrier, wherein the carrier contains aliphatic or aromatic amine groups or sulphide groups.

The invention accordingly provides a process for preparing an alkanone and/or alkanol by oxidizing an alkane with 3-30 C-atoms, using oxygen, to form an alkyl hydroperoxide, followed by a decomposition of the resulting alkyl hydroperoxide in the presence of a metal compound immobilized on a carrier, and is characterized in that the carrier carries aliphatic or aromatic amine groups or sulphide groups.

The carrier preferably has groups with the following structure:

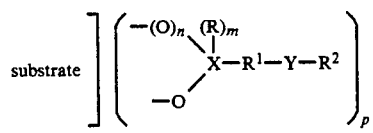

where the substrate is silica, alumina, titanate, and where $n=0$, 1 or 2 and $m=0$, 1 or 2, where $n+m=2$ p is greater than 1, $X=Si$, Ti or Zr $R=H$ or $C_{1-12}$ alkyl or alkoxy $R^1=C_{1-18}$ alkyl, aryl, alkaryl $Y=S$ or $NR^3$ $R^2, R^3$: H, $C_{1-12}$ alkyl, or $R^4—Z—R^5$, where $R^4=C_{2-12}$ alkyl $Z=NR^6$ or S $R^5, R^6=H$, or $C_{1-6}$ alkyl, and where $R^1$ may comprise ether groups and $R^2, R^3, R^4, R^5$ and $R^6$ may additionally contain 1 or 2 ether, alcohol or carboxyl groups.

Preferably, the carrier used having aliphatic or aromatic amine groups or sulphide groups, is a carrier having groups with the formula—$R^1—Y—R^2$ where $R^1$, Y and $R^2$ are as described above.

The substrate preferably has on its surface groups capable of reacting with an organosilicon compound, an organotitanium compound or with another organometallic compound. Hydroxyl groups are particularly suited. An aminoalkyl compound, for instance, is then linked to the substrate by means of a covalent bond, via, for instance, a silicon compound. The substrate used may, for instance, be silica, zeolite, aluminasilica mixtures or titanium dioxide.

As X, for instance, any of Si, Ti or Zr is highly suited, while preference is given to the use of silicon.

R is preferably methoxy, ethoxy, methyl, ethyl, isopropoxy, n-propoxy, propyl or butoxy.

$R^1$ is, for instance, an alkyl residue such as ethyl, propyl, isopropyl, n-butyl, (1- or 2-methylpropyl, pentyl, cyclopentyl, n-hexyl, 2-methylpentyl, cyclohexyl, octyl, benzyl, phenyl or 2,2-diphenylpropyl. Preference is given to the use of a $C_{2-6}$ alkyl, particularly ethyl or propyl, because these are commercially available. $R^1$ may further contain inert hetero groups, such as ether-oxygen atoms.

For Y, either sulphur or nitrogen is highly suited, with preference for nitrogen. The sulphide of amine groups may be primary, secondary or (with the amine) also tertiary, as long as a valence remains for a proper coordination with a catalytic metal from Periodic Table groups IB, IVB, VB, VIB, VIIB and VIII. With a secondary sulphide or amine or tertiary amine, $R^2$ and $R^3$ are independently, for instance methyl, ethyl, propyl, i-propyl, butyl, 2-methylpropyl, t-butyl, hexyl, octyl or, for instance, 2-aminoethyl, 2-sulphidoethyl or 3-aminopropyl. Preferably $R^2$ and, as the case may be, $R^3$, represent H, $C_{1-6}$ alkyl or $R^4$—Z—$R^5$, wherein $R^4$ is a $C_{2-8}$ alkyl and Z is $NR^5$ or S and $R^5$ and $R^6$ are independently, H or $C_{1-8}$ alkyl. $R^2$ is preferably particularly H or $R^4$—$NH_2$ where $R^4$ is $C_{2-3}$ alkyl.

The said carrier having an amino group or a sulphide group, may also be a weakly basic ion exchanger such as, for instance, a polystyrene (crosslinked with divinylbenzene) carrying —$NR_2$ groups (where R=H, methyl or ethyl) or a resin carrying an S—R group.

The catalytic metal complex or metal salt used is preferably a complex or salt of a metal from the fourth period of groups IB, IVB, VB, VIB, VIB or VIII of the periodic system. Examples of highly suitable metals are cobalt, chromium, vanadium, molybdenum, ruthenium, titanium, manganese, iron, and preferably cobalt, chromium, vanadium, molybdenum, and iron. The preferred metal compound comprises a complex or salt of a metal of this group. Of course, mixtures of metals can be used also. For the periodic system reference is made to the first page of the 'Handbook of Chemistry and Physics', 70th edition (1989-1990), the notation used is according to the 'ICAS version'.

Such catalysts are known, and may be used for the oxidation of cyclohexane as described in J. Org. Chem. Vol. 56 (1991) pp. 1981-1983. However, an oxidation reaction is essentially different from an alkylhydroperoxide decomposition reaction. Furthermore, the use of the catalyst in the present invention is advantageous in that the catalyst is unexpectedly more stable than prior art heterogeneous catalysts.

The catalyst can be made by impregnating said carrier having the aliphatic or aromatic amine or sulphide groups, with such a metal compound wherein metal compound at least a part of the ligands has a weaker bond with the metal than an amine or sulphide group. The metal ion then complexes with the amine and/or sulphide group of the carrier, so that an unexpectedly stable catalyst is thereby obtained. This is unexpected, because, for instance, a porphyrin-cobalt complex on a carrier had proved to lack long-term stability. The metal compound is preferably a metal salt or metal complex soluble in, for instance, alcohol or water, so that the carrier can be easily impregnated.

Said carrier having aliphatic or aromatic amine or sulphide groups is commercially available, or it can be synthesized by dispersing a substrate such as, for instance, silica or an alumina-zeolite in an organic liquid such as, for instance, reethanol, ethanol, THF, dioxane, DMSO, toluene, cyclohexanol or acetone. To this dispersion an organofunctional silane or titanate can then be added. The silane used may, for instance, be 3-aminopropyltrimethoxy- silane, N-methyl-3-amino-propyl-trimethoxysilane, 3-aminopropyl-tris(2-methoxypropyl-tri-methoxysilane, N-amino-ethyl-3-aminopropyltrimethoxysilane, N-aminoethyl-3-amino-propylmethyl-dimethoxysilane, 3-mercaptopropyl-trimethoxysilane, 3-mercaptopropyl-triethoxysilane, 3-mercaptopropyl-methyl-dimethoxysilane, p-aminophenyltriethoxysilane. The titanate used may, for instance, be neoalkoxytri(m-aminophenyl)titanate.

The organosilane or titanate compound is usually reacted with the substrate for a period of 10-300 minutes at a temperature ranging from 0° to 150° C. Optimum conditions can easily be selected by the person skilled in the art. The product can then be filtered off, washed and, if so desired, can also be dried. The product can also, without further purification, be further processed.

A metal compound is added to the resulting carrier with the aliphatic or aromatic amine groups or sulphide groups. To this end the carrier is preferably dispersed in an agent in which the metal compound dissolves. The mixture is preferably stirred. The process may be performed in a fixed bed. The complexing of the metal to the carrier containing the amine or sulphide group usually takes 10-300 min and is conveniently effected between 0° and 100° C., preferably between 20°-50° C. However, the time and temperature are not critical and can for practical reasons be chosen rather indiscriminately.

The mixture containing alkylhydroperoxide in a solvent is preferably obtained by oxidizing an alkane with 3-30 carbon atoms using oxygen.

In the process according to the invention the oxidation of the alkane is effected in the liquid phase in the manner known in the art using, for instance, air, pure oxygen or a mixture of oxygen and inert gas at temperatures of 120°-200° C., particularly 140°-180° C., for, for instance, 0.1 to 24 hours, preferably 0.5 to 24 hours. In the process, for instance, from 1-50% of the alkane is converted, which amount may also be kept between 1 and 25%. The pressure in this oxidation process is not critical and is generally between 0.4 and 5 MPa (4 and 50 bar.)

The oxidation of the alkane is preferably carried out in the absence of substances promoting the decomposition of the alkyl hydroperoxide which is formed, such as transition metal compounds and, therefore, for this reaction preference is given to the use of a reactor with an inert inner wall, for instance an inner wall of passivated steel, aluminum, glass, enamel and similar materials. If, nonetheless, the use of an oxidation catalyst is desired, the amount of transition metal must preferably be very small, for instance in the order of 1-10 parts by weight per million. As oxidation catalyst, compounds of, for instance, cobalt, chromium, manganese, iron, nickel, copper or mixtures thereof can be used. The immobilized organometallic complexes described in this application are also suitable.

Optionally, the mixture containing the alkylhydroperoxide can be concentrated by evaporating some or all of the alkane. The alkane may be replaced by another solvent such as alcohol. However, preferably the alkylhydroperoxide is dissolved in its corresponding alkane. Furthermore, the mixture may comprise alkanol and alkanone.

The decomposition of the alkyl hydroperoxide in the oxidation mixture is effected by means of the immobilized metal complexes according to the invention. The decomposition catalyst can be used in various ways. As it is immobilized on a carrier, both slurry reactors and, for instance, packed beds can be used to effect the conversion of the alkyl hydroperoxide. The heat of reaction released in the decomposition must be adequately received and carried off to guarantee a proper process temperature control. This can very effectively be done by using slurry reactors. During the decomposition, the desired temperature can then, for instance, be maintained by reflux cooling to carry off at least a part of the heat. No recirculation of evaporated products will then be required, which has a slightly favorable effect on the yield of desired product. In such a situation, the amount of immobilized complex to be used is, for instance, 5–250 ppm of catalyst metal calculated on the oxidation mixture. Preference is given to the use of more than 10 ppm. and less than 150 ppm.

The process can also advantageously be carried out in a fixed bed reactor, because a relatively high catalyst concentration can then be reached. This is particularly advantageous if hydroperoxide mixtures are used having a relatively low concentration.

The temperature during the decomposition is generally in the range of 25°–200° C., preferably between 50° and 120° C. Preferably, the temperature is at least 20° C. lower than the temperature used in the oxidation step, and more preferably, at least 40° C. lower. In the decomposition, the pressure employed is usually slightly lower than in the oxidation. The decomposition is preferably effected in the presence of oxygen. This improves the yield of K/A mixture.

Depending on the concentration of the transition metal on the carrier, the concentration of the hydroperoxide and the temperature, the decomposition usually takes between 5 and 300 minutes. Preferably the residence time of the reaction mixture in a decomposition reactor is kept between 15 and 120 minutes, although this is not critical. By means of simple analyses, a person skilled in the art can determine if any hydroperoxide is left in a treated mixture.

Prior to the decomposition of the hydroperoxide in the oxidation mixture, the oxidation mixture can be treated, if so desired, with water or an aqueous alkali metal hydroxide or alkali metal carbonate solution for the removal and/or neutralization of the acids formed in the oxidation, for instance to a pH of the aqueous phase of 8–13.

The reaction mixture obtained in the decomposition of the hydroperoxide is an alkanone or alkanol in a solvent, where the solvent generally is the corresponding alkane. Furthermore side products may be present. The mixture can then be further processed by subjecting the organic phase, after washing with water if so desired, to a distillation process while recovering alkane (as well as the alkanol and alkanone) for recycling. Thereafter, distillation of the desired products, alkanol and alkanone, can be performed. Generally, the alkanol and the alkanone will be separately obtained.

The $C_{3-30}$ alkane used may, for instance, be propane, 2-methylpropane, cycloheptane, cyclohexane, methylbenzene, ethylbenzene, 2-propylbenzene, phenylcyclohexane, cyclohexene, diphenylmethane, phenylcyclododecane, 4-tert.butyl-1-cycloheptylbenzene, 2-isopropylnapthalene, fluorene, 1,8-dinethylfluorene, or 1,2-dicyclohexylmethane. The alkane may thus have aromatic groups and ethylenically unsaturated group substituents. The alkane may be branched, linear and/or cyclic.

The process is particularly suited for the oxidation of cycloalkanes with 4–18 carbon atoms, and more particularly for the oxidation of cyclohexane, cyclooctane and cyclododecane, the reaction products of the cyclohexane oxidation being particularly suited for use in the preparation of either caprolactam (for nylon-6) or adipic acid (for nylon-6,6). The resulting cyclohexanol and cyclohexanone obtained after distillation of the mixture of alkane with cyclohexanol and cyclohexanone have been found without further processing to be sufficiently pure for further conversion into caprolactam.

The invention will be further elucidated by means of the following examples.

SYNTHESIS

Preparation of the Carrier (Ex. I–IV)

Example I

To 100 g of a silica (Grace SG524, BET surface area=540 m$^2$/g, particle size=1–3 mm) 500 ml methanol was added at room temperature. This suspension was stirred for 15 minutes. Thereafter, 250 g 3-aminopropyltrimethoxysilane was added. The suspension was stirred at room temperature for 1 hour. After filtration, the solid was washed with 200 ml toluene. This washing was repeated twice. The product was subsequently dried. The carbon content of the modified silica thus obtained (type A) is 63 g/kg.

In the modification of silicas with different BET surface areas, the amount of the aminosilane was adjusted in direct proportion to the surface area of the silica (for, for instance, for a silica with a BET surface area of 390 m$^2$/g, 180 g of the silane was used). Reaction times and temperature remained the same. Other solvents such as ethanol and toluene, for instance, were found not to have a significant effect on the result. When using a silica with a different particle size distribution, the results were found to be the same. Other silanes could also be used, as is shown by the examples below.

Example II

To 100 g of a silica (Grace 1000MP, BET surface area=50 m$^2$/g, particle size=1–3 mm) 500 ml methanol was added at room temperature. This suspension was stirred for 15 minutes. Thereafter, 25 g N-2-aminoethyl-3-aminopropyltrimethoxysilane was added. The suspension was stirred at room temperature for 1 hour. After filtration, the solid was washed with 200 ml toluene. This washing was repeated twice. The product was subsequently dried. The carbon content of the modified silica thus obtained (type B) was 8 g/kg.

Example III

To 50 g of a silica (Grace SG254, BET surface area=540 m$^2$/g, particle size=0.8–1.4 mm) 250 ml methanol was added at room temperature. This suspension was stirred for 15 minutes. Thereafter, 25 g 3-mercaptopropyltrimethoxysilane was added. The suspension was stirred at room temperature for 1 hour. After filtration, the solid was washed with 200 ml methanol. This washing was repeated twice. The product was subsequently dried. The sulphur content of the modified silica thus obtained (type C) was 32 g/kg.

Example IV

To 50 g of a silica (Grace SG254, BET surface area=540 m$^2$/g, particle size=0.8–1.4 mm) 250 ml ethanol was added at room temperature. This suspension was stirred for 15 minutes. Thereafter, 25 g p-aminophenyl-bimethoxysilane was added. The suspension was stirred at room temperature for 1 hour. After filtration, the solid was washed with 200 ml ethanol. This washing was repeated twice. The product was subsequently dried. The nitrogen content of the modified silica thus obtained (type D) was 28 g/kg.

Generally, it may be said that, if silanes are used having the general formula $R^1—Si(OR^2)_3$, where $R^2$ stands for a methyl group or an ethyl group, the above procedure can be used to modify a silica surface.

Addition of Catalyst Metal (Ex. V–XI)

Example V

To 10 g of type A 165 ml of a solution of Co(II)-acetate-tetrahydrate in water (100 g/l) was added. The suspension was stirred for 3 hours at a temperature of 47° C. After filtration, the solid was washed with 400 ml water. The washing procedure was repeated twice. After drying, the resulting silica (type A-Co-1) contained 33 g Co/kg.

By varying (particularly) the reaction time and the temperature it was found that, on the basis of type A silicas, catalysts could be prepared having a cobalt content ranging from 1% to 8%. In the table below, a number of these results are shown.

TABLE 1

Survey of type A catalysts

| Code | Particle size (mm) | Metal content (%(wt)) |
|---|---|---|
| A-Co-1 | 1–3 | 3.3 |
| A-Co-2 | 1–3 | 2.4 |
| A-Co-3 | 1–3 | 4.6 |
| A-Co-4 | 1–3 | 7.8 |
| A-Co-5 | 1–3 | 3.6 |
| A-Co-6 | 0.8–1.4 | 2.4 |
| A-Co-7 | 0.03–0.1 | 3.2 |
| A-Co-8 | 0.8–1.4 | 1.2 |

Example VI

To 10 g of type B 165 ml of a solution of Co(II)-acetate-tetrahydrate in water (100 g/l) was added. The suspension was stirred for 3 hours at a temperature of 47° C. After filtration, the solid was washed with 400 ml water. The washing procedure was repeated twice. After drying, the silica thus obtained (type B-Co-1) contained 3 g Co/kg.

Example VII

To 10 g of type C 200 ml of a solution of Co(II)-acetate-tetrahydrate in water (100 g/l) was added. The suspension was stirred at room temperature for 5 hours. After filtration, the solid was washed with 400 ml water. The washing procedure was repeated twice. After drying, the silica thus obtained (type C-Co-1) contained 13 g Co/kg.

Example VIII

To 10 g of type D 165 ml of a solution of Co(II)-acetate-tetrahydrate in water (100 g/l) was added. The suspension was stirred for 4 hours at a temperature of 47° C. After filtration, the solid was washed with 400 ml water. The washing procedure was repeated twice. After drying, the silica thus obtained (type D-Co-1) contained 45 g Co/kg.

Example IX

To 15 g of type A 100 ml of a solution of $Cr(NO)_3 \cdot 9 H_2O$ in water (33 g/l) was added. The suspension was stirred at room temperature for 18 hours. After filtration, the solid was washed with 400 ml water. The washing procedure was repeated twice. After drying, the silica thus obtained (type A-Cr-1) contained 14 g Cr/kg.

Example X

To 15 g of type A 100 ml of a solution of Fe(II)-sulphate-heptahydrate in water (12 g/l) was added. The suspension was stirred at room temperature for 18 hours. After filtration, the solid was washed with 400 ml water. The washing procedure was repeated twice. After drying, the silica thus obtained (type A-Fe-1) contained 29 g Fe/kg.

Example XI

To 15 g of type A 100 ml of a solution of $Cr(NO)_3 \cdot 9 H_2O$ (33 g/l) and $COSO_4$ (23 g/l) in water was added. The suspension was stirred at room temperature for 18 hours. After filtration, the solid was washed with 400 ml water. The washing procedure was repeated twice. After drying, the silica thus obtained (type A-Co-Cr-1) contained 13 g Cr/kg and 12 g Co/kg.

Batch Process Experiments

Example XII

To 50 g of a cyclohexane oxidation mixture containing 200 mmoles cyclohexyl hydroperoxide (CHHP), 60 mmoles cyclohexanol (OL) and 30 mmoles cyclohexanone (ON) per kilogram, 0.5 g A-Co-1 was added at a temperature of 75° C. This mixture was stirred at said temperature until all CHHP was decomposed. The decomposition was followed by means of an iodometric titration. The first order reaction rate constant k was $2.8 \times 10^{-3}$ kg sol/(min $\times$ g cat). The selectivity, based on the OL+ON formed in relation to the converted CHHP, was 112%. The OL/ON ratio was 1.6. The catalyst could be used a plurality of times without any significant decline of activity.

Comparative Experiment A

Example XII was repeated, the homogeneous catalyst being Co-2-ethylhexanoate (70 ppm Co in solution). The k was $2.0 \times 10^{-2}$ min$^{-1}$ for the first 20 minutes of the decomposition. After 20 minutes, the catalyst showed a strong decline of activity. The selectivity to OL+ON was 91.6%. The OL/ON ration was 2.2. Re-use was not possible.

Examples XIII–XXV

Example XII was repeated with the other catalysts. The results are shown in the table below.

TABLE 2

Results with different catalysts

| Example | Catalyst Code | Particle Size (mm) | Metal Content (% (wt)) | k (kg sol/ (min × g cat)) |
|---|---|---|---|---|
| XIII | A-Co-1 | 1–3 | 3.3 | $2.79 \times 10^{-3}$ |
| XIV | A-Co-2 | 1–3 | 2.4 | $1.99 \times 10^{-3}$ |
| XV | A-Co-3 | 1–3 | 4.6 | $2.43 \times 10^{-3}$ |
| XVI | A-Co-4 | 1–3 | 7.8 | $1.28 \times 10^{-3}$ |
| XVII | A-Co-5 | 1–3 | 3.6 | $2.94 \times 10^{-3}$ |
| XVIII | A-Co-6 | 0.8–1.4 | 2.4 | $6.01 \times 10^{-3}$ |
| XIX | A-Co-7 | 0.03–0.1 | 3.2 | $46.9 \times 10^{-3}$ |

TABLE 2-continued

| Example | Catalyst Code | Particle Size (mm) | Metal Content (% (wt)) | k (kg sol/ (min × g cat)) |
|---|---|---|---|---|
| XX | B-Co-1 | 1–3 | 0.3 | 3.02 × 10$^{-3}$ |
| XXI | B-Co-1 | 1–3 | 1.3 | 1.13 × 10$^{-3}$ |
| XXII | D-Co-1 | 1–3 | 4.5 | 2.93 × 10$^{-3}$ |
| XXIII | A-Cr-1 | 1–3 | 1.4 | 2.00 × 10$^{-3}$ |
| XXIV | A-Fe-1 | 1–3 | 2.9 | 0.04 × 10$^{-3}$ |
| XXV | A-Co-Cr-1 | 1–3 | 1.2/1.3 | 0.65 × 10$^{-3}$ |

Comparative Experiment B

Example XXIV was repeated, the catalyst being Fe-(II)sulphate-heptahydrate (70 ppm in relation to the liquid). In consequence of the fact that the Fe catalyst did not dissolve in the oxidate, the decomposition rate was insignificant.

Comparative Experiment C

Example XXIII was repeated, the catalyst being Cr-2-ethylhexanoate (70 ppm in solution). The k was only 0.008 min$^{-1}$. The selectivity to OL+ON was 91.7%. The OL/ON ratio was only 0.2. The catalyst could not be used again.

Example XXVI

Example XII was repeated, except that now air was passed through the reaction mixture. This caused the yield to rise to 114%. The OL/ON ratio fell to 1.3.

Example XXVII

To 50 g of a cyclododecane oxidation mixture containing 400 mmoles cyclododecyl hydroperoxide (CDHP), 70 mmoles cyclododecanol (DOL) and 40 mmoles cyclododecanone (DON) per kilogram, 0.5 g A-Co-5 was added at a temperature of 75° C. This mixture was stirred at said temperature until all CDHP was decomposed. The decomposition was followed by means of an iodometric titration. The first order reaction rate constant k was 2.94×10$^{-3}$ kg sol/min×g cat. The selectivity, based on the DOL+DON formed in relation to the converted CDHP, was 108%. The DOL/DON ratio was 1.4. The catalyst could be used a plurality of times without any significant decline of the activity.

Continuous Process Experiments

Example XXVIII

Into a column with a diameter of 3 cm and a length of 10 cm, 29 g A-Co-8 was introduced. Over this column, the oxidate mentioned in example XII was pumped at a velocity of 20 g/hour. The temperature in the column was kept at 75° C. In this manner, a conversion was reached of more than 80%. The catalyst was tested for more than 1000 hours and still did not exhibit any deactivation; moreover, analyses of the organic effluent revealed that the Co concentration in this effluent was less than 2 ppb. The selectivity to OL+ON was >100%.

Comparative Experiment D

To 10 g of a silica (Grace SG254, BET surface area 540 m$^2$/g, particle size 1–3 mm) 165 ml of a solution of Co(II)-acetate-tetrahydrate in water (100 g/l) was added. The suspension was stirred for 19 hours at a temperature of 85° C. After filtration, the solid was washed with 400 ml water. The washing procedure was repeated twice. After drying, the resulting silica contained 92 g Co/kg. Into a column having a diameter of 3 cm and a length of 10 cm 7 g of this catalyst was introduced. The oxidate mentioned in example XII was pumped over this column at a velocity of 40 g/hour. The temperature in the column was kept at 80° C. In the first instance, a conversion was reached in this manner of >80%. The catalyst, however, was clearly de-activated such that after 1000 hours, its activity had fallen to <20%. The selectivity to OL+ON was 89%.

Comparative Experiment E

On a silica of type A (Grace SG239, BET surface area 390 m$^2$/g, particle size 1–3 mm) a Co-tetra-sulpho-chloride-phthalocyanine was bonded (see, inter alia, EP-A-367326). The Co-content of the catalyst thus obtained was 5 g/kg. Into a column having a diameter of 3 cm and a length of 10 cm, 10 g of this catalyst was introduced. The oxidate mentioned in example XII was pumped over this column at a velocity of 20 g/hour. The temperature in the column was kept at 75° C. In the first instance, a conversion was reached in this manner of >90%. The conversion then rapidly fell to 20% to remain stable thereafter (duration of test >500 hours).

Example XXIX

Example XXVIII was repeated using catalyst A-Cr-1. At a conversion of 75%, the catalyst still showed no de-activation after 1000 hours.

We claim:
1. A process for preparing an alkanone and/or alkanol by decomposing an alkyl hydroperoxide in a solvent in the presence of a metal compound immobilized on a carrier, said metal is at least one catalytic metal selected from the group consisting of cobalt, chromium, vanadium, molybdenum, ruthenium, titanium, manganese, iron, and mixtures thereof, said carrier having aliphatic or aromatic amine groups or sulphide groups, said carrier having the following structure,

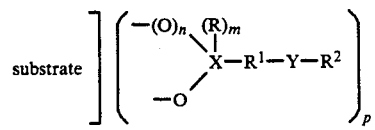

wherein said structure
the substrate is silica, alumina, or titanate,
n represents 0, 1, or 2 and m represents 0, 1, or 2 and where n+m is 2,
p is greater than 1,
X is Si, Ti or Zr,
R is H or C$_{1-12}$ alkyl or alkoxy
R$^1$ is C$_{1-18}$ alkyl, aryl, alkaryl
Y is S or NR$^3$, and
R$^2$ and R$^3$ each independently represent H, C$_1$–C$_{12}$ alkyl, or
R$^4$—Z—R$^5$, where
R$^4$ is C$_2$–C$_{12}$ alkyl
Z is NR$^6$ or S, and
R$^5$ and R$^6$ independently represent H, or C$_1$–C$_6$ alkyl, and where R$^1$ may contain ether groups and R$^2$, R$^3$, R$^4$, R$^5$ and R$^6$ may independently additionally contain 1 or 2 ether, alcohol or carboxyl groups.

2. A process according to claim 1, wherein the substrate is silica.

3. A process according to claim 1, wherein X is Si.

4. A process according to claim 1, wherein $R^1$ is $C_2$-$C_6$ alkyl.

5. A process according to claim 1, wherein $R^2$ is H or $R^4$—$NH_2$ with the proviso that $R^4$ is $C_2$-$C_3$ alkyl.

6. A process according to claim 1, wherein $R^3$ is H.

7. A process according to claim 1, wherein said metal is introduced as a salt or complex soluble in a dispersant and complexed to said carrier having amine groups or sulphide groups.

8. A process for preparing an alkanone and/or alkanol by oxidizing an alkane, using oxygen, to form an alkyl hydroperoxide in a solvent, followed by decomposing the resulting alkyl hydroperoxide in the presence of a metal compound immobilized on a carrier, wherein said metal is at least one catalytic metal selected from the group consisting of metals from Group IB, Group IVB, Group VB, Group VIB, Group VIIB and Group VIII of the Periodic Table, and said carrier contains aliphatic or aromatic amine groups or sulphide groups of the formula:

$$-R^1-Y-R^2$$ 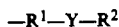

wherein said formula
$R^1$ is $C_{1-18}$ alkyl, aryl, or alkaryl;
Y is S or $NR^3$; and
$R^2$ and $R^3$ are independently selected from the group consisting of H, $C_1$-$C_{12}$ alkyl, and $R^4$—Z—$R^5$, wherein
$R^4$ is $C_2$-$C_{12}$ alkyl,
Z is $NR^6$ or S, and
$R^5$ and $R^6$ independently represent H or $C_1$-$C_6$ alkyl, and
$R^1$ may contain ether groups and $R^2$, $R^3$, $R^4$, $R^5$ and $R^6$ may independently additionally contain 1 or 2 ether, alcohol or carboxyl groups.

9. A process according to claim 8, wherein said alkane has 3-30 carbon atoms, said oxidation is conducted at a temperature of 120° C. to 200° C. and at a pressure of 0.4 MPa to 5 MPa, and said decomposition is conducted at a temperature of 25° C. to 200° C.

10. A process according to claim 8, wherein said carrier has the formula:

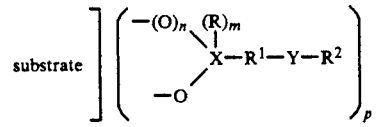

wherein said formula
the substrate is silica, alumina, or titanate
n represents 0, 1 or 2 and m represents 0, 1 or 2 and where n+m is 2,
p is greater than 1,
X is Si, Ti or Zr,
R is H or $C_{1-12}$ alkyl or $C_{1-12}$ alkoxy,
$R^1$ is as defined in claim 8,
Y is as defined in claim 8, and
$R^2$ and $R^3$ are as defined in claim 8.

11. A process according to claim 8, wherein said metal is selected from the group consisting of cobalt, chromium, vanadium, molybdenum, ruthenium, titanium, manganese, iron and mixtures thereof.

12. A process according to claim 10, wherein the substrate is silica.

13. A process according to claim 12, wherein X is Si.

14. A process according to claim 10, wherein the substrate is silica, X is Si, and Y is $NR^3$ with the proviso that Z is $NR^6$.

15. A process according to claim 8, wherein $R^1$ is $C_2$-$C_6$ alkyl.

16. A process according to claim 8, wherein $R^2$ is H or $R^4$—$NH_2$ with the proviso that $R^4$ is $C_2$-$C_3$ alkyl.

17. A process according to claim 8, wherein $R^3$ is H.

18. A process according to claim 8, wherein said metal is introduced as a salt or complex soluble in a dispersant and complexed to said carrier having amine groups or sulphide groups.

19. A process for preparing an alkanone and/or alkanol by decomposing an alkyl hydroperoxide in a solvent at a temperature of 25° C. to 200° C. in the presence of a metal compound immobilized on a carrier, wherein said metal is at least one catalytic metal selected from the group consisting of metals from Group IB, Group IVB, Group VB, Group VIB, Group VIIB and Group VIII of the Periodic Table, and said carrier contains aliphatic or aromatic amine groups or sulphide groups of the formula:

$$-R^1-Y-R^2$$ 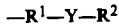

wherein said formula
$R^1$ is $C_{1-18}$ alkyl, aryl, or alkaryl;
Y is S or $NR^3$; and
$R^2$ and $R^3$ are independently selected from the group consisting of H, $C_1$-$C_{12}$ alkyl, and $R^4$—Z—$R^5$, wherein
$R^4$ is $C_2$-$C_{12}$ alkyl,
Z is $NR^6$ or S, and
$R^5$ and $R^6$ independently represent H or $C_1$-$C_6$ alkyl, and
$R^1$ may contain ether groups and $R^2$, $R^3$, $R^4$, $R^5$ and $R^6$ may independently additionally contain 1 or 2 ether, alcohol or carboxyl groups.

20. A process according to claim 19, wherein said carrier has the formula:

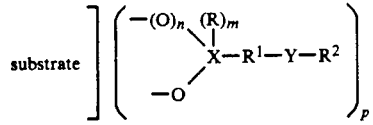

wherein said formula
the substrate is silica, alumina or titanate,
n represents 0, 1 or 2 and m represents 0, 1 or 2 and where n+m is 2,
p is greater than 1,
X is Si, Ti, or Zr,
R is H or $C_{1-12}$ alkyl or $C_{1-12}$ alkoxy,
$R^1$ is as defined in claim 19,
Y is as defined in claim 19,
$R^2$ and $R^3$ are as defined in claim 19.

21. A process according to claim 20, wherein the substrate is silica, X is Si, and Y is $NR^3$ with the proviso that Z is $NR^6$, said metal is selected from the group consisting of cobalt, chromium vanadium, molybdenum, ruthenium, titanium, manganese, iron and mixtures thereof, $R^1$ is $C_2$-$C_6$ alkyl and $R^2$ is H or $R^4$—$NH_2$ with the proviso that $R^4$ is $C_2$-$C_3$ alkyl.

* * * * *